(12) United States Patent
Sommer et al.

(10) Patent No.: US 8,455,691 B2
(45) Date of Patent: Jun. 4, 2013

(54) PROCESS FOR THE PURIFICATION OF AROMATIC AMINES

(75) Inventors: Knut Sommer, Krefeld (DE); Franz-Ulrich Gehlen, Krefeld (DE); Peter Lehner, Mülheim/Ruhr (DE); Andre Düx, Brühl (DE); Benie Marotz, Düsseldorf (DE)

(73) Assignee: Bayer MaterialScience AG, Leverkusen (DE)

( * ) Notice: Subject to any disclaimer, the term of this patent is extended or adjusted under 35 U.S.C. 154(b) by 1149 days.

(21) Appl. No.: 12/228,722

(22) Filed: Aug. 15, 2008

(65) Prior Publication Data

US 2009/0065347 A1 Mar. 12, 2009

(30) Foreign Application Priority Data

Aug. 18, 2007 (DE) .......................... 10 2007 039 091

(51) Int. Cl.
*C07C 211/00* (2006.01)
(52) U.S. Cl.
USPC .......................................... 564/305; 564/336
(58) Field of Classification Search
None
See application file for complete search history.

(56) References Cited

U.S. PATENT DOCUMENTS

| | | | |
|---|---|---|---|
| 2004/0242924 A1* | 12/2004 | Zehner et al. | 562/517 |
| 2005/0080294 A1 | 4/2005 | Renner et al. | |
| 2007/0203364 A1* | 8/2007 | Dugal et al. | 564/423 |
| 2007/0238901 A1 | 10/2007 | Dugal et al. | |

FOREIGN PATENT DOCUMENTS

| | | |
|---|---|---|
| DE | 3414714 C2 | 6/1986 |
| JP | 4935341 A | 4/1974 |
| JP | 8295654 A | 11/1996 |
| JP | 2005350388 A | 12/2005 |

OTHER PUBLICATIONS

JP-2005-350388 Machine Translation, 2005, 1-5.*
JP=-080295654 Machine Translation, 1996, 1-4.*
Gerd Kaibel, "Distillation Columns with Vertical Partitions", Chem Eng. Technol. (month unavailable) 1987, 10, p. 92-98.
G. Kaibel, "Industrieller Einsatz von Trennwandkolonnen and thermisch gekoppelten Destillationskolonnen", Chemie Ingenieur Technik, (month unavailable) 2003, 75, p. 1165-1166.

* cited by examiner

*Primary Examiner* — Johann R Richter
*Assistant Examiner* — Clinton Brooks
(74) *Attorney, Agent, or Firm* — Lyndanne M. Whalen

(57) ABSTRACT

Aromatic amines which have been obtained by reduction of aromatic nitro compounds are purified by mixing the crude amine obtained after phase separation with an aqueous, alkali metal hydroxide solution and subsequent distillation of this mixture over a distillation column. The distillation column has at least an upper and a lower rectifying part and a stripping part. The bottom product of the distillation column is partly to completely sluiced out and is partly evaporated in a main evaporator and at least one downstream re-evaporator and partly recycled back into the column.

11 Claims, 5 Drawing Sheets

PROCESS FOR THE PURIFICATION OF AROMATIC AMINES

BACKGROUND OF THE INVENTION

The present invention relates to a process for the purification of aromatic amines which are obtained by reduction of aromatic nitro compounds. Aromatic amines as used herein means those compounds which carry at least one amino group on an aromatic ring. The latter may be substituted or fused with other aromatic rings.

Aromatic amines are important intermediates which must be available inexpensively and in large amounts. For the preparation of aniline, for example, installations with very high capacities must therefore be built. Aniline is, for example, an important intermediate in the preparation of methylenediphenyl-diisocyanate (MDI) and is prepared on a large industrial scale as a rule by catalytic reduction of nitrobenzene with hydrogen, as described, e.g., in DE-A 2201528; DE-A 3414714; U.S. Pat. No. 3,136,818; EP-B1 0 696 573; and EP-B1 0 696 574.

In catalytic reductions for the preparation of aromatic amines, water and organic secondary components are formed in addition to the desired product(s). These organic secondary components ("by-products") must be separated off before further use of the aromatic amine(s). These by-products include "low-boiling substances", i.e. compounds or azeotropically boiling mixtures of individual components having boiling points below that of the amine to be prepared, and "high-boiling substances", i.e. compounds or azeotropically boiling mixtures of individual components having boiling points above that of the amine to be prepared. In the case of the reduction of nitrobenzene to aniline (b.p.=184° C.), examples are benzene (b.p.=80° C.) for the group of low-boiling substances and diphenylamine (b.p.=302° C.) for the group of high-boiling substances. These two impurities mentioned as examples can be easily separated off by distillation because their boiling points are very different from that of the amine to be prepared ($\Delta T_B$=104 K and 118 K respectively). Separation of those secondary components which have boiling points very similar to that of the amine to be prepared is considerably more problematic, because the outlay on distillation will be considerably higher. In the case of the reduction of nitrobenzene, the separation of phenol (b.p.=182° C.) and the target product aniline (b.p.=184° C.) in particular is a great challenge for distillation technology. The difficulty of this separation is evident from the fact that long distillation columns with a high number of separating stages and high reflux ratios with correspondingly high outlay on investment and energy are used. Compounds with phenolic hydroxyl groups, i.e. compounds which carry at least one hydroxyl group on an aromatic ring, can generally be problematic in the working up of aromatic amines. In the case of aniline, in addition to the phenol already mentioned, the various aminophenols are also problematic.

Therefore, the purification of aromatic amines is not trivial, and is of great industrial importance. Recent approaches are directed, in particular, to resolving the problems mentioned in connection with compounds having phenolic hydroxyl groups. One approach is to convert the compounds with phenolic hydroxyl groups into the corresponding salts by reaction with suitable bases. The salts are non-volatile compounds which are considerably easier to separate off. For this purpose, alkali metal hydroxides are employed for an extraction, or an alkali metal hydroxide is added during the distillation.

JP-A-49-035341 describes a process in which the amine to be purified, aniline, is brought into contact with solid alkali metal hydroxides in a fixed bed and only then is passed into the distillation, or the distillation is carried out in the presence of the solid alkali metal hydroxide in amounts of 0.1-3 percent by weight, based on the amount of aniline to be distilled. The separating off of critical components, such as the aminophenols, is simplified by this means. However, disadvantages of this process are the use of high molar excesses of the solid alkali metal hydroxides in relation to the acidic secondary components to be removed and the impossibility of precise metering of the alkaline compounds. This can lead to corrosion problems, precipitates and high-viscosity bottom product phases in the distillation column in the event of over-metering, and to an incomplete removal of the critical components in the event of under-metering.

JP-A-08-295654 describes, as an alternative to removal of compounds with phenolic hydroxyl groups from aniline by distillation, an extraction with dilute aqueous sodium hydroxide solution or potassium hydroxide solution (concentration 0.1-0.7 percent by weight, based on the weight of the alkali metal hydroxide solution) by which most of the phenol is transferred as alkali metal phenolate into the aqueous phase, and the phenolate is separated off by the subsequent phase separation. For effective reduction of the phenol content, a molar ratio of NaOH:phenol in the range of 3:1-100:1 is required. Disadvantages of this process are the high NaOH consumption (molar excesses), the production of very large amounts of waste water containing alkali metal phenolate—as a result of the low concentration of the alkali metal hydroxide solutions—which leads to additional disposal costs, and an additional outlay on investment for the extraction.

US-A-2005 080294 describes a process for separating off compounds with phenolic hydroxyl groups ("phenolic compounds") from aromatic amines, in which before the distillation a base is added to the amine to be purified in a molar ratio of from 1:1 to 4:1, based on the "phenolic compounds", optionally in the presence of polyols. US-A-2005 080294 does not teach in detail what happens to the salts which are formed in the reaction of the "phenolic compounds" with the bases. In Example 6, it is merely mentioned that excess solid KOH is dissolved by addition of polyethylene glycol (PEG). What consequences are associated with this is not to be found in US-A-2005 080294. US-A-2005 080294 does not go into detail at all with respect to the salts of the "phenolic compounds" themselves.

However, salts, excess base, and the salts of the compounds with phenolic hydroxyl groups, in general are only sparingly soluble in aromatic amines, so that there is great danger that they will become concentrated beyond the solubility limit in the distillation column, in the bottom product of the distillation column and/or in the evaporator of the distillation, and then precipitate out. Such solid precipitates can severely interfere with the distillation process, so that an interruption in the distillation operation becomes necessary. Such interruption can lead to considerable difficulties and even to losses in production in large-scale industrial processes continuously. US-A-2005 080294, however, is not concerned with the problem of reliability and service life of the process. The person skilled in the art also does not learn from US-A-2005 080294 that the presence of the salts formed during the reaction of the compounds with phenolic hydroxyl groups with the bases can lead to deposition of solids, fouling and/or a high increase in viscosity during the distillation. US-A-2005 080294 does not go into details of the distillation technique at all. The person skilled in the art therefore does not learn from US-A-2005 080294 how he is to solve these problems which occur with high probability. US-A-2005 080294 teaches only the optional addition of PEG in order to dissolve excess solid KOH. Such an addition of PEG into the distillation, however, is economically unacceptable because of the high capacities in the preparation of aromatic amines (in particular aniline). The use of the process described in US-A 2005 080294 in a continuous production process is not described.

JP-A-2005 350388 is concerned quite generally with improving the working up of aniline. A process is described in which some of the bottom product of the aniline distillation column is removed and transferred into the gas phase separately, i.e. in a second evaporator which differs from the actual evaporator of the column. The gas phase obtained in this way is recycled into the pure aniline column; high-boiling contents which cannot be evaporated are separated off. In this manner, the temperature of the aniline distillation column can be kept relatively low and amounts of impurities can be reduced; the aniline loss in the separating off of high-boiling substances is likewise reduced. A disadvantage of this process is that before the actual aniline distillation column, low-boiling substances and water are separated off separately by an additional distillation in a dewatering column in a process which is expensive in terms of apparatus. JP-A-2005 350388 does not mention the particular problems with compounds with phenolic hydroxyl groups for the distillation. It is therefore also not to be ascertained from this Japanese patent application whether separating these off from the target product aniline can be improved with the process described there.

EP-A-07075103 describes a process for the purification of aniline by addition of an aqueous alkali metal hydroxide solution before or during the distillation. EP-A-07075104 describes a process for the purification of aniline by extraction with aqueous alkali metal hydroxide solution. In contrast to the present Application, neither of these published disclosures teaches partial or complete sluicing out of the bottom product of the aniline distillation column and partial evaporation thereof via two evaporators ($E^1$) and ($E^2$) connected in series or parallel. By the procedure of the present invention described in more detail herein after, a maximum depletion of the valuable amine in the bottom product of the distillation column is achieved with a minimum outlay on apparatus and energy.

SUMMARY OF THE INVENTION

The object of the present invention is therefore to provide a process for the purification of aromatic amines which improves the separating off of the compounds with phenolic hydroxyl groups, without causing problems such as deposition of solids, fouling and/or a high increase in viscosity during the distillation, improves the product yield and the service life and at the same time ensures a low outlay on apparatus, with a low energy consumption.

This object has been achieved by a process for the purification of aromatic amines prepared by reduction of aromatic nitro compounds in which the product mixture obtained from the reduction is subjected to the specific purification steps in the sequence specified herein.

DETAILED DESCRIPTION OF THE INVENTION

Figure 1:
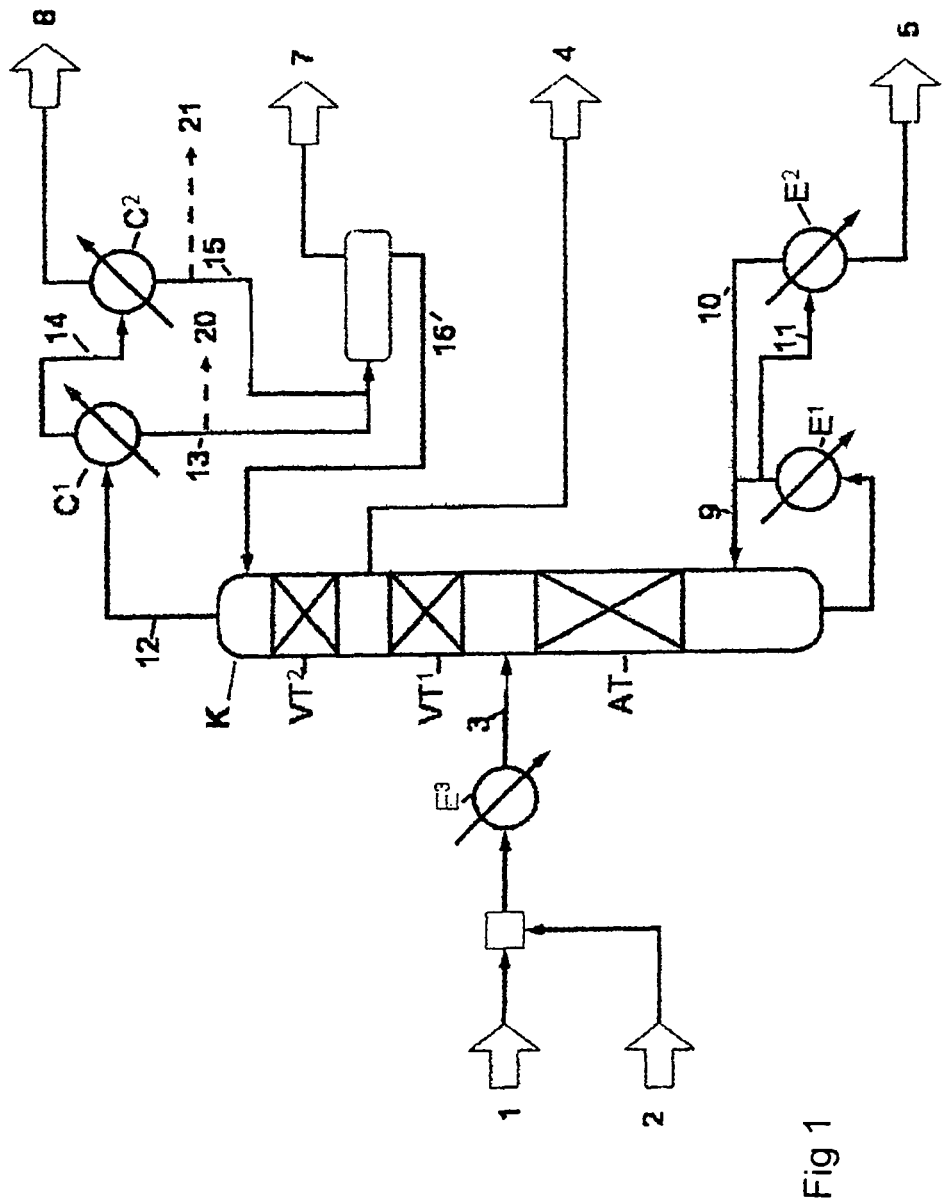
FIG. 1 is a diagram of the distillation column with two-stage energy supply in the bottom of the column.

In the present invention, purification of the aromatic amines is carried out by freeing the product mixture obtained from the reduction from the majority of the water of reaction formed during the reduction by a phase separation in accordance with any of the techniques known to the person skilled in the art. The organic phase obtained by this phase separation ("crude amine") is then passed together with an aqueous solution of an alkali metal hydroxide into a distillation column. In this distillation column, low-boiling substances are removed as the overhead product, high-boiling substances are removed as the bottom product and the purified aromatic amine ("pure amine") is removed in a side stream. The column is composed of at least three sections, namely an upper rectifying part, a lower rectifying part and a stripping part. The outflow from the stripping part is partly evaporated with the aid of a main evaporator. A portion of the stream of the non-evaporated liquid is then concentrated in a re-evaporator, the gas phase is recycled back into the column, and the liquid phase is partly or completely sluiced out. A maximum depletion of the valuable amine in the bottom product of the column is ensured in this manner with a minimum outlay on apparatus and energy.

More specifically, in the process of the present invention, the product mixture obtained from the reduction is subjected to the following purification steps in the following sequence:

I. separating off of the water of reaction formed during the reduction by phase separation, wherein, in the crude amine obtained in this way, a residual content of water corresponding to the solubility of water in the crude amine is established, which depends on the pressure and temperature and the precise composition of the crude amine and which is between 2 and 10 percent by weight, preferably between 4 and 10 percent by weight, based on the weight of the crude amine, II. mixing of the crude amine obtained from step I with an aqueous solution of an alkali metal hydroxide, III. feeding of the mixture from step II into a distillation column (K), wherein this distillation column (K) comprises at least an upper rectifying part ($VT^2$), a lower rectifying part ($VT^1$) and a stripping part (AT), IV. partial to complete removal of the bottom product from the region below the stripping part (AT), V. partial evaporation of this bottom product removed from step IV in a main evaporator ($E^1$) and at least one downstream re-evaporator ($E^2$), wherein the re-evaporator ($E^2$) is operated at a higher temperature than the main evaporator ($E^1$), down to a residual content of aromatic amine in the outflow of the re-evaporator ($E^2$) of from 0 to 98 percent by weight, VI. complete recycling of the gas phases obtained in step V and partial recycling of the liquid phases into the column (K), either below or above the stripping part (AT), and partial or complete sluicing out of the liquid phase obtained in the re-evaporator ($E^2$).

The process according to the invention is particularly advantageous if amines of the formula

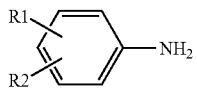

in which R1 and R2 independently of one another denote hydrogen, methyl or ethyl, wherein R1 can additionally denote amino, are to be purified. The invention is very particularly advantageous if aniline obtained by reduction of nitrobenzene is to be purified.

The process according to the invention is advantageous especially if the alkali metal hydroxides are employed as aqueous solutions and the content of alkali metal hydroxide in these solutions is >0.7 percent by weight and ≦55 percent by weight.

The process of the present invention is particularly advantageous if the absolute amount of alkali metal hydroxides added is in a range of $$0.01 < n(MOH)/[\Sigma\{i \cdot n(Ar(OH)_i)\}] < 1.5$$

wherein
n=molar amount of substance,
M=alkali metal,
$Ar(OH)_i$=compound with i phenolic hydroxyl groups and i denotes a natural number.

The term $$[\Sigma\{i \cdot n(Ar(OH)_i)\}]$$

accordingly designates the sum of all the phenolic hydroxyl groups in the crude amine, for example the sum of the hydroxyl groups from phenol and the various aminophenols. For determination of this term, determination of the concentration of the compounds with phenolic hydroxyl groups in the crude amine before mixing with the aqueous alkali metal hydroxide solution is necessary. This determination is made by any of the usual analytical methods, preferably by gas chromatography.

The process of the present invention is particularly advantageous if the distillation column (K) is operated under an absolute pressure of from 10 to 1,000 mbar and with a reflux ratio of from 0.05 to 3.

The process of the present invention is also particularly advantageous if the re-evaporator ($E^2$) is operated under the same pressure as the main evaporator ($E^1$).

In another advantageous embodiment of the process of the present invention, the re-evaporator ($E^2$) is also suitable for processing of deposit-forming products, i.e. those products which tend towards formation of deposits on surfaces. Possible re-evaporators are, e.g., plate or tube bundle heat exchangers with forced circulation and thin layer, falling film or spiral tube evaporators.

In the process of the present invention, it is advantageous if the re-evaporator ($E^2$) is flushed with water, preferably water of reaction, at regular intervals. How often such cleaning operations are conducted depends on the type of evaporator used.

It is also advantageous in carrying out the process of the present invention to extract the bottom product outflow of the main evaporator ($E^1$) with water, preferably water of reaction.

The process of the present invention is also advantageous if very low water contents (e.g., $c(H_2O) \ll 1,000$ ppm) in the pure amine are desired because this aim can be achieved in a very simple manner by designing the distillation column (K) as a partition column.

The general principle of the functioning of partition columns is described, for example, in G. Kaibel, "Distillation Columns with Vertical Partitions", *Chem. Eng. Technol.* 1987, 10, 92-98 and G. Kaibel, "Industrieller Einsatz von Trennwandkolonnen und thermisch gekoppelten Destillationskolonnen", *Chemie Ingenieur Technik* 2003, 75, 1165-1166.

The process according to the invention is described in greater detail below.

The aromatic amine(s) are prepared in the process of the present invention by catalytic reduction of the corresponding nitro compound(s). The nitro compounds used as starting materials are those compounds in which the aromatic ring carries a nitro group or several nitro groups instead of the amino group(s) of the target compound.

In the process of the present invention, the reduction of the nitro compounds to give the desired aromatic amines can be carried out by any of the methods which can be conducted industrially, preferably by reduction with hydrogen (hydrogenation), more preferably by gas phase hydrogenation.

The gas phase hydrogenation is most preferably carried out on fixed-position, heterogeneous supported catalysts, such as Pd on aluminum oxide or carbon supports, in fixed bed reactors under an absolute pressure of 1-50 bar and a temperature in the range of 150-600° C. under adiabatic conditions in a circulating gas procedure, i.e. with recycling of hydrogen which is not reacted during the hydrogenation. Such a process is described, for example, in EP-B1 0 696 573 and EP-B1 0 696 574.

The water of reaction formed during the reduction of the aromatic nitro compound to give the amine is first separated off by a phase separation using any of the techniques known to the person skilled in the art. Such separation depletes the water content of the crude amine to a value which corresponds to the solubility of water in the crude amine under the given conditions (pressure, temperature, composition), this water of reaction residual content is between 2 and 10 percent by weight, preferably between 4 and 10 percent by weight. No removal of other low-boiling substances takes place in this stage.

The purification steps subsequent to the phase separation are explained in detail with reference to FIGS. 1-5. These Figures show only illustrative embodiments of the process according to the invention and are not to be understood as being the only embodiments of the present invention.

FIG. 1 shows how the crude amine (1) obtained in this way is mixed with an aqueous alkaline solution, preferably, an aqueous alkali metal hydroxide solution (2)—for substantial conversion of compounds with phenolic hydroxyl groups into the corresponding alkali metal salts—in a feed heater ($E^3$) and is passed as feed (3) directly into a distillation column (K). Alkali metal hydroxide solutions (2) which can be employed are solutions which include any alkali metal hydroxide, preferably, sodium hydroxide solution or potassium hydroxide solution, most preferably sodium hydroxide solution. However, an aqueous solution of any of the alkali metals can in principle be used. Other water-soluble basic compounds, such as alkaline earth metal hydroxides or alkali metal or alkaline earth metal carbonates or bicarbonates, could in principle also be employed instead of the alkali metal hydroxides. For economic reasons, however, alkali metal hydroxides are preferred.

The content of alkali metal hydroxide in the alkaline solution is >0.7 percent by weight and ≦55 percent by weight, preferably ≧1 percent by weight and ≦50 percent by weight, most preferably ≧5 percent by weight and ≦35 percent by weight. The absolute amount of alkali metal hydroxide to be added is chosen so that it is in a range of $$0.01 < n(MOH)/[\Sigma\{i \cdot n(Ar(OH)_i)\}] < 1.5,$$

preferably, $$0.50 < n(MOH)/[\Sigma\{i \cdot n(Ar(OH)_i)\}] < 1.0,$$

most preferably $$0.90 < n(MOH)/[\Sigma\{i \cdot n(Ar(OH)_i)\}] < 1.0.$$

By using the lowest amount of excess alkali metal hydroxide (in preferred embodiments of the process according to the invention, excess alkali metal hydroxide is avoided completely), the formation of solid deposits in the distillation column, in the bottom product of the distillation column and/or in the evaporator of the distillation apparatus which interfere considerably with the distillation process or can even render it completely impossible is prevented.

The distillation column (K) is operated under an absolute pressure of from 10 to 1,000 mbar, preferably from 50 to 800 mbar, most preferably from 100 to 500 mbar, and with a reflux ratio of from 0.05 to 3, preferably from 0.1 to 2, most preferably from 0.1 to 0.9. In this specific case, the ratio of the amount of liquid introduced at the upper end of the lower rectifying part (segment ($VT^1$) to the amount of liquid removed in the side stream (4) is called the reflux ratio. The distillation column (K) comprises at least a lower rectifying part ($VT^1$), an upper rectifying part ($VT^2$) and a stripping part (AT). The high-boiling substances are separated off in the lower rectifying part ($VT^1$). These arrive, together with some of the amine, in the stripping part (AT), where they are concentrated. Low-boiling substances and water are concentrated in the upper rectifying part ($VT^2$), and the vapors (12) are removed above the head and, for separation of low-boiling substances and water, are passed through n condensers ($C^1$), ($C^2$), ... ($C^n$) (the fact that in the figure only two condensers, which are connected via line (14), are shown is not to be understood as a limitation), wherein n is a natural number and can be in the range of from 1 to 5, preferably from 1 to 3, most preferably from 1 to 2. The n condensates obtained from the n condensers (in this case stream 13 and 15) are combined and subjected to a phase separation. By this means, the aqueous phase (7) is discharged and either recycled into another position in the process, preferably into the phase separation described in step I., or disposed of. The organic phase (16) substantially comprising the aromatic amine is recycled into the head of the distillation column (K). In a particular embodiment, a part of the n condensates (20 and 21) is sluiced out for the purpose of additional separation and removal of low-boiling substances. In a further embodiment, which is known to the person skilled in the art as the dephlegmator procedure, low-boiling substances are partly to completely (0.01-100%) sluiced out with the residual vapor stream (8). The pure amine is removed in a side stream (4) between the two rectifying parts ($VT^1$) and ($VT^2$).

The outflow from the stripping part (AT) is partly evaporated with the aid of the main evaporator ($E^1$). A part stream or the total stream of the liquid (11) which has not been evaporated is then concentrated in a re-evaporator ($E^2$), the gas phase (10) being recycled back into the column and the liquid phase (5) being sluiced out. The re-evaporator ($E^2$) is operated here at a temperature which is up to 100 K higher than the main evaporator ($E^1$). The bottom product of the distillation column (K) is concentrated effectively and gently in this manner. The alkali metal salts of the compounds with phenolic hydroxyl groups which are formed become concentrated in the bottom product of the distillation column (K) or of the main evaporator ($E^1$). This concentration preferably takes place to just below the solubility limit, which depends on the physical framework conditions (pressure, temperature, composition). (Any small residual amounts of compounds with phenolic hydroxyl groups which have not reacted, i.e. still have their OH function(s), still present are separated off together with the high- or low-boiling substances, depending on the particular boiling point.) The second evaporator stage is operated under the same pressure as the first. The high-boiling substances in the outflow of the first evaporator stage (11), however, are concentrated still further, i.e. the re-evaporator ($E^2$) is preferably operated at a higher temperature than the main evaporator ($E^1$). Although the concentration of the bottom product of the re-evaporator ($E^2$) can be operated to beyond the solubility limit of the salts of the compounds with phenolic hydroxyl groups, at this point no problems due to solid deposits possibly occurring are to be feared because in preferred embodiments of the process according to the invention the re-evaporator ($E^2$) is suitable for processing deposit-forming products, is particularly easy to clean and is flushed with water, preferably water of reaction, at regular intervals. The sluicing out from the re-evaporator ($E^2$) is carried out by discharge devices known to the person skilled in the art, such as pumps or screws. Possible embodiments for the re-evaporator ($E^2$) include plate or tube bundle heat exchangers with forced circulation or thin layer, falling film or spiral tube evaporators, which are known to the person skilled in the art. By this procedure, a maximum depletion of the valuable amine in the bottom product of the distillation column is achieved with a minimum outlay for apparatus and energy. The residual amine contents in the outflow of the re-evaporator ($E^2$) are adjusted to values of from 0 to 98 percent by weight, preferably 15 to 80 percent by weight, more preferably 20 to 60 percent by weight and most preferably 20 to 40 percent by weight.

The gas phase (9) obtained from the main evaporator ($E^1$) is recycled back into the distillation column (K) below the stripping part (AT). The gas phase (10) obtained from the re-evaporator ($E^2$) is likewise passed back into the distillation column (K) below the stripping part (AT) of the distillation column (K), and the bottom outflow (5) of the re-evaporator ($E^2$) is disposed of.

Figure 2:
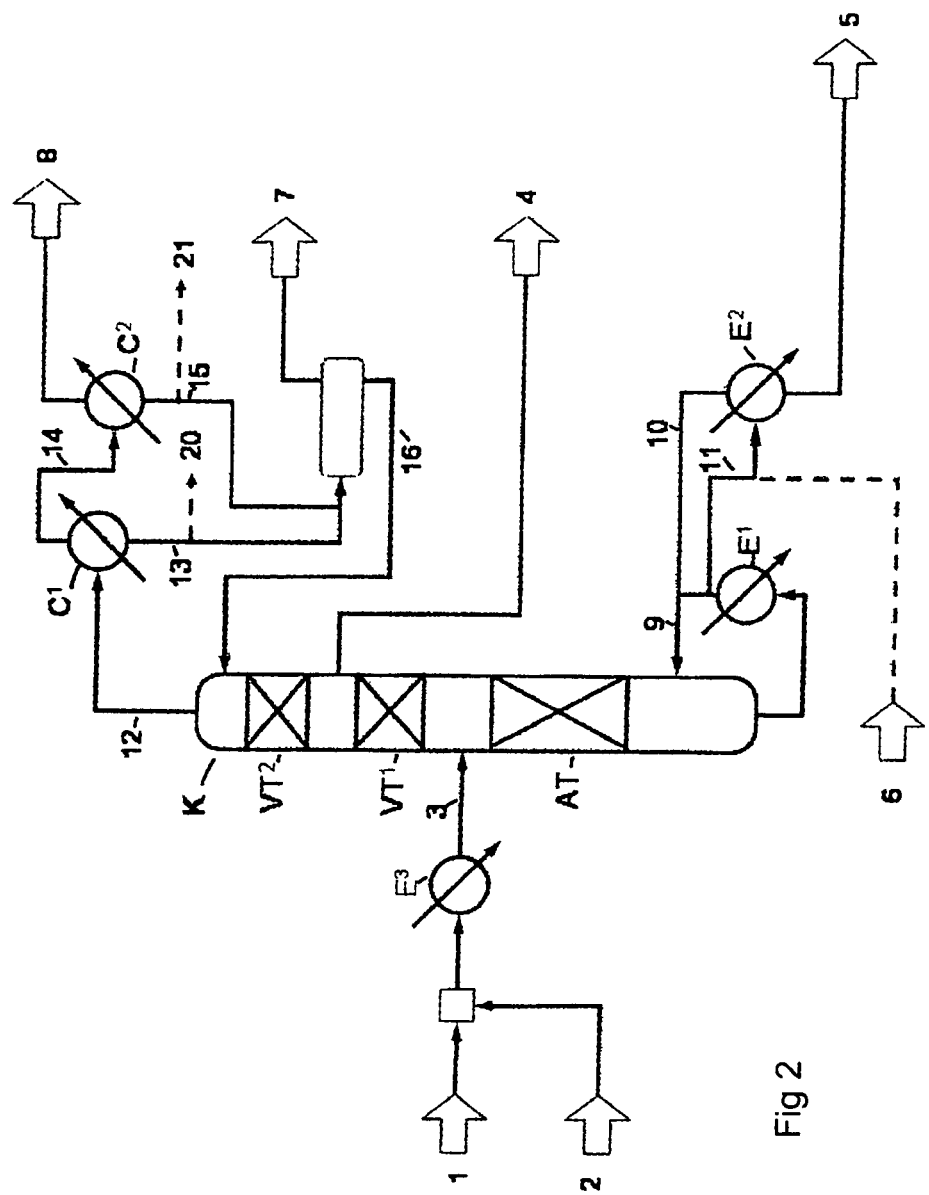
FIG. 2 is a diagram of the distillation column with two-stage energy supply in the bottom of the column and $H_2O$ addition in the second evaporator stage.

FIG. 2 shows an alternative embodiment of the distillation column described in FIG. 1. In FIG. 2, water is introduced into the re-evaporator ($E^2$) via a feed stream (6) in order to remove any deposits present. In this case the flushing solution is disposed of together with the remaining residue (5).

Figure 3:
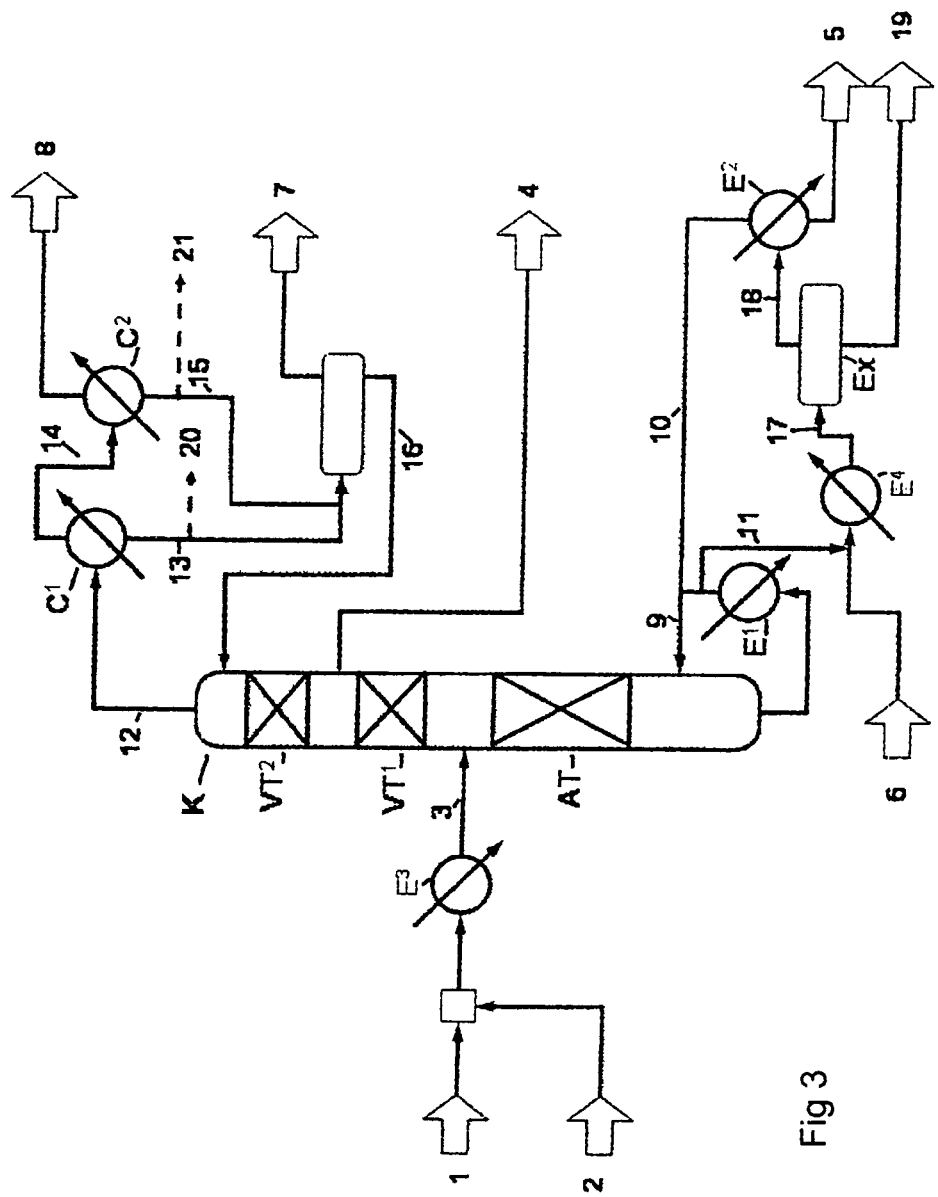
FIG. 3 is a diagram of the distillation column with two-stage energy supply in the bottom of the column and intermediate extraction.

FIG. 3 illustrates an alternative embodiment of the apparatus illustrated in FIG. 2 in which the bottom outflow (11) is extracted with water (6), preferably water of reaction. The alkali metal salts are washed out of the organic phase here and transferred into the aqueous phase. For this, after passing through a cooling unit ($E^4$), the mixture (17) is passed into an extractor (Ex), where the organic and aqueous phase are then separated by means of a phase separation known to the person skilled in the art. The organic phase (18) obtained in this way is passed into the re-evaporator ($E^2$) and the aqueous phase (19) is disposed of with the remaining waste water. In this manner, a trouble-free continuous operation of the installation is ensured and the formation of precipitates, e.g. of alkali metal phenolates, which interfere considerably in the distillation process or can even render it completely impossible is avoided.

If particular requirements are imposed on the water content of the purified amine (e.g. $c(H_2O) << 1,000$ ppm), the distillation column is preferably designed as a partition column (dividing wall distillation column).

Figure 4:
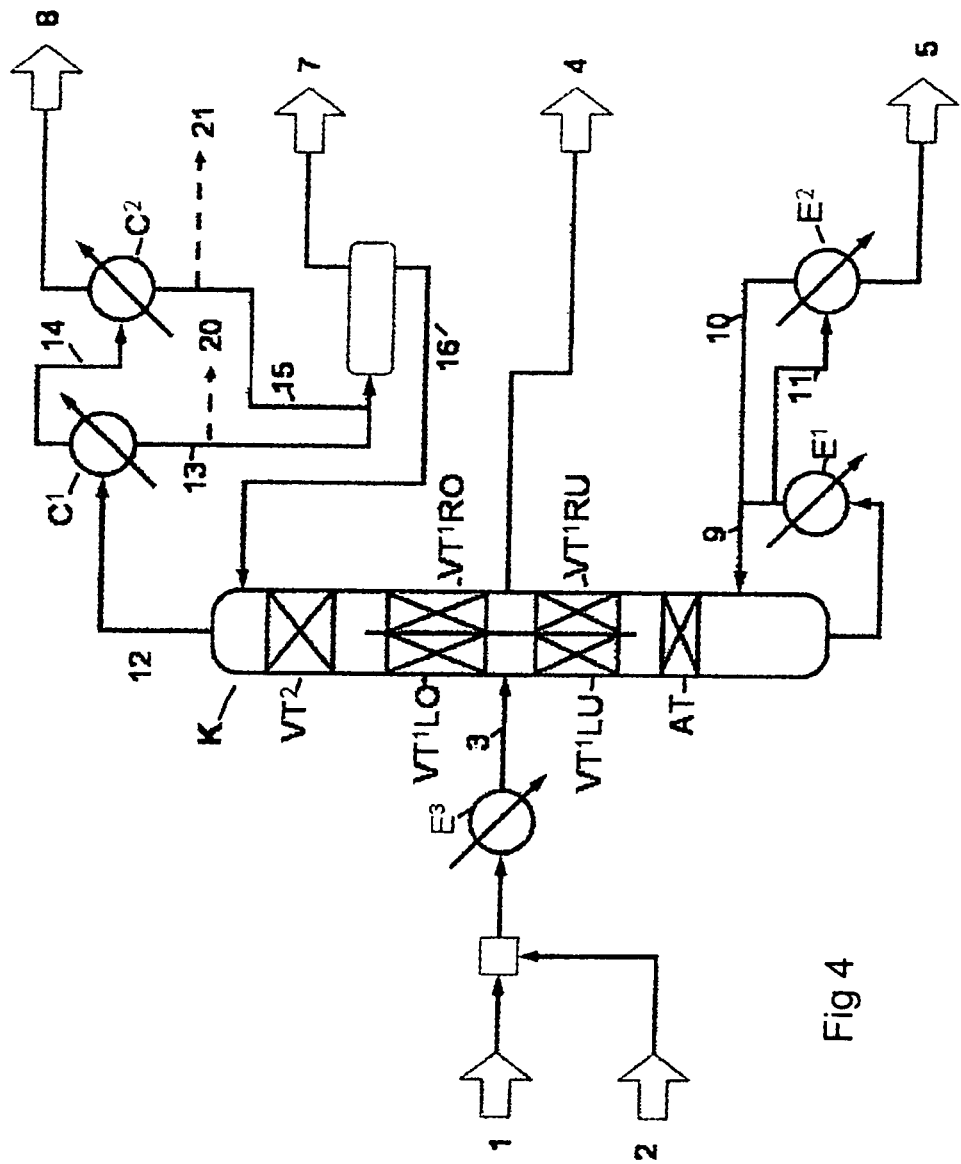
FIG. 4 is a diagram of the partition column with two-stage energy supply in the bottom of the column.

FIG. 4 is therefore an alternative design to the distillation column (K) from FIG. 1, wherein, however, a partition column is employed. The partition column comprises, as is also the case in the process variant according to FIG. 1, an upper rectifying part (VT²) and a stripping part (AT) and, instead of the lower rectifying part (VT¹), at least four sections in the region of the partition, so that the total number of sections in this embodiment is at least six. In the region of the partition, the section (VT¹LO) serves to deplete high-boiling compounds contained in the feed stream (3), the section (VT¹LU) serves to deplete low-boiling substances contained in the feed stream (3), in particular water, the section (VT¹RO) serves to further deplete low-boiling substances contained in the liquid flowing out of (VT²), so that these do not enter into the amine, and the section (VT¹RU) serves to deplete high-boiling substances contained in the vapors coming out of (AT). The introduction of energy is analogous to the process variant corresponding to FIG. 1.

Figure 5:
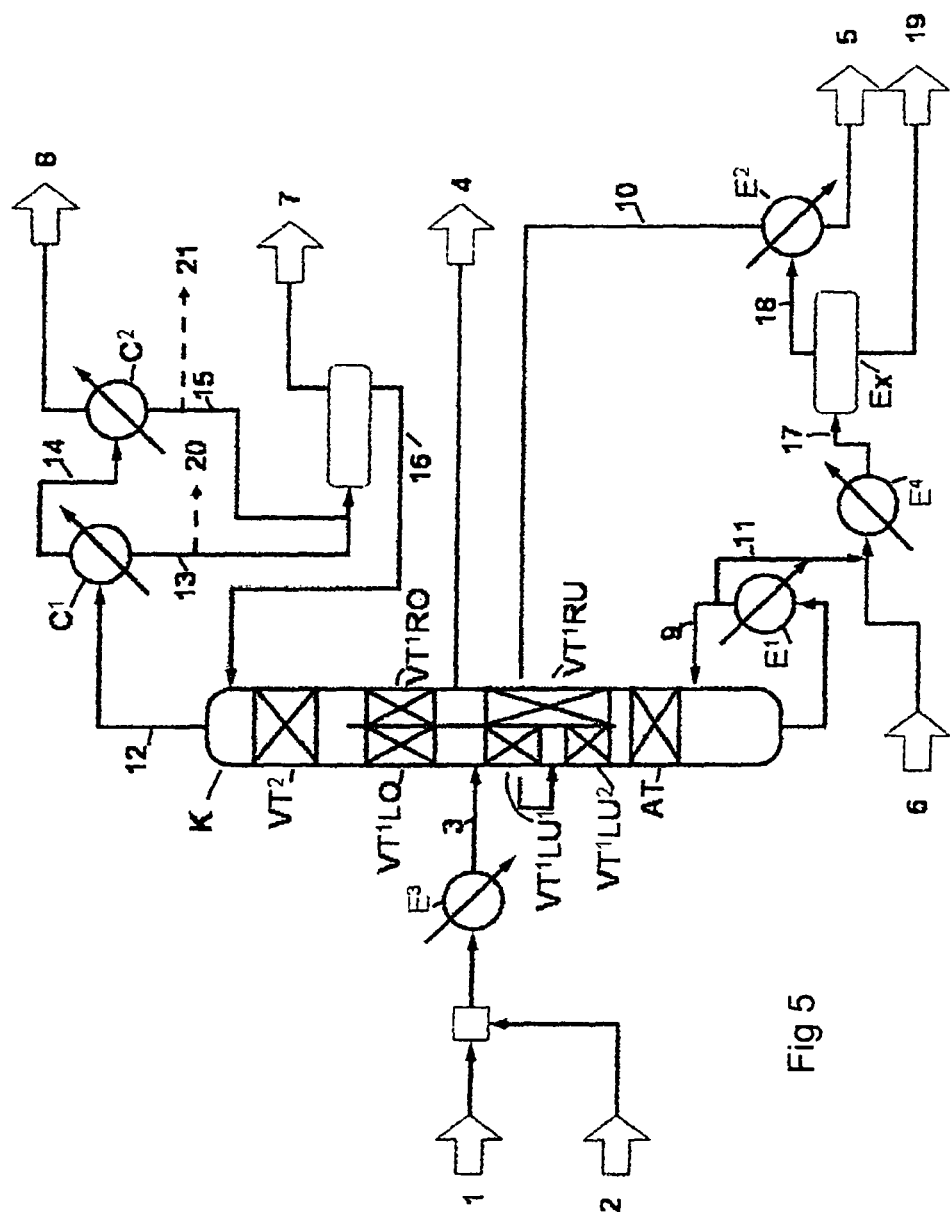
FIG. 5 is a diagram of the partition column with two-stage energy supply in the bottom of the column and intermediate extraction.

An alternative to the procedure according to FIG. 4 is illustrated in FIG. 5. In FIG. 5, as in FIG. 3, an extraction device (Ex) is provided for extraction of the bottom outflow with water, preferably water of reaction. The partition column comprises, as also in the process variant according to FIG. 3, an upper rectifying part (VT²) and a stripping part (AT). In contrast to the process outlined in FIG. 3, instead of the lower rectifying part (VT¹) in the region of a partition, there are at least five sections, so that the total number of sections in this embodiment is at least seven. In the region of the partition, the section (VT¹LO) serves to deplete high-boiling compounds contained in the feed stream (3), the sections (VT¹LU¹) and (VT¹LU²) serve to deplete low-boiling substances contained in the feed stream (3) or in the vapor stream (10), in particular water, the section (VT¹RO) serves to further deplete low-boiling substances contained in the liquid flowing out of (VT²), so that these do not enter into the amine, and a section (VT¹RU) serves to deplete high-boiling substances contained in the vapours coming out of (AT). The introduction of energy is analogous to the process variant corresponding to FIG. 3. The vapor (10) from the re-evaporator (E²) is fed in between the sections (VT¹LU¹) and (VT¹LU²) of the partition column because of their water content. By this means, the water contained in the vapor (10) of the re-evaporator (E²) is prevented from entering into the amine.

The process described above is a practicable solution to the separation problem encountered with compounds with phenolic hydroxyl groups and ensures a maximum depletion of the valuable amine in the bottom product of the distillation column with a minimum outlay for apparatus and energy.

EXAMPLES

Example 1

According to the Invention

Distillation Under 360 mbar and R/E 0.3 (From a Simulation Calculation)

A crude aniline stream (1.994 kg/h) composed of:

| Component | Content in percent by weight |
| --- | --- |
| Aniline | 97.600 |
| Water | 2.000 |
| Benzene | 0.065 |

| Component | Content in percent by weight |
| --- | --- |
| Phenol | 0.077 |
| Diphenylamine | 0.139 |
| Other secondary components | 0.119 | was mixed with a 10% strength sodium hydroxide solution (6.1 g/h). The mixture obtained in this way was fed to a distillation column (diameter: 70 mm) having:

1. an upper rectifying part with 10 theoretical stages;
2. a lower rectifying part with 12 theoretical stages; and
3. a stripping part with 12 theoretical stages.

The column was operated under a pressure of 360 mbar. The condensation system of the column was in two stages. The first stage was operated at a condensation temperature of 65° C. and the second stage at a temperature of 45° C. The condensate obtained was cooled to 30° C. and fed to a phase separation. The organic (at the same time also the heavy) phase was introduced back at the head of the column.

Below the upper rectifying part, aniline (1.95 kg/h) was obtained with a purity of 99.94% and the following impurities:

| Component | Content in percent by weight |
| --- | --- |
| Water | 0.0371 |
| Benzene | 0.0018 |
| Phenol | 0.0040 |
| Other secondary components | 0.0171 |

The ratio of the product stream removed to the liquid stream which flowed out of the upper rectifying part was 0.23, which resulted in a reflux ratio of 0.3.

The energy was introduced into the column in two stages. In a first stage, the liquid flowing out of the column was concentrated to the solubility limit of the sodium phenolate (3 percent by weight) in a falling film evaporator (main evaporator). The aniline concentration was depleted to 92 percent by weight here. The bottom temperature was 152° C. The bottom product was then fed to a thin layer evaporator (re-evaporator) for further concentration and to minimize the aniline losses. The aniline content was depleted to 49.3 percent by weight here, as a result of which the sodium phenolate concentration increased to 19.5 percent by weight. The bottom temperature rose to 165° C.

Example 2

According to the Invention

Distillation Under 150 mbar and R/E=0.8 (From Simulation Calculation)

Under conditions otherwise identical to those used in Example 1, the column was operated under an overhead pressure of 150 mbar. The condensation system of the column was in two stages. The first stage was operated at a condensation temperature of 45° C. and the second stage at a temperature of 35° C. The condensate obtained was cooled to 30° C. and fed to a phase separation. The organic (at the same time the heavy) phase was introduced back at the head of the column.

Below the upper rectifying part, aniline (1.95 kg/h) with a purity of 99.96% and the following impurities were obtained:

| Component | Content in percent by weight |
| --- | --- |
| Water | 0.0200 |
| Benzene | 0.0009 |
| Phenol | 0.0017 |
| Other secondary components | 0.0174 |

The ratio of the product stream removed to the liquid stream which flowed out of the upper rectifying part was 0.44, which corresponds to a reflux ratio of 0.8.

The energy was introduced into the column in two stages. In a first stage, the liquid flowing out of the column was concentrated to the solubility limit of the sodium phenolate (3 percent by weight) in a falling film evaporator (main evaporator). The aniline concentration was depleted to 92 percent by weight here. The bottom temperature was 129° C. The bottom product was then fed to a thin layer evaporator (re-evaporator) for further concentration and to minimize the aniline losses. The aniline content was depleted to 49.3 percent by weight here, as a result of which the sodium phenolate concentration increased to 19.5 percent by weight. The bottom temperature rose to 141° C.

Example 3

According to the Invention

Distillation in the Laboratory Under 400 mbar with a Thin Layer Evaporator as the Re-Evaporator A feed mixture (see the table below for the composition) which represents the composition of the outflow of the main evaporator ($E^1$) was separated thermally by means of a one-stage evaporation under an absolute pressure of 400 mbar and an overhead temperature of 150° C. in a thin layer evaporator, which serves here as the re-evaporator ($E^2$). For this, a feed stream of 800 g/h was fed continuously via a metering pump into the thin layer evaporator. The heating of the evaporator (approx. 160° C.) was adjusted such that 86-87 percent by weight of the feed stream was obtained as the distillate. The distillate was removed completely after a one-stage condensation. The liquid mass stream (13-14 percent by weight) which remained was removed at the bottom of the thin layer evaporator.

Results of the laboratory studies on working up of the feed mixture in a thin layer evaporator were as follows:

| | Content in percent by weight | | |
| --- | --- | --- | --- |
| Component | in the feed | in the distillate | in the bottom product |
| Aniline | 94.428 | 99.600 | 60.000 |
| Phenol | 0.044 | 0.000 | 0.600 |
| Diphenylamine | 2.528 | 0.400 | 17.000 |
| Sodium phenolate | 3.000 | 0.000 | 22.400 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the purification of an aromatic amine prepared by reduction of an aromatic nitro compound in which a product mixture is obtained by reducing the aromatic nitro compound comprising subjecting the product mixture to steps I. through VI:
   I. separating off the water of reaction formed during the reduction by phase separation, wherein, in the crude amine obtained in this way, a residual content of water corresponding to the solubility of water in the crude amine is established, which depends on the pressure and temperature and the precise composition of the crude amine and which is between 2 and 10 per cent by weight, based on the weight of the crude amine,
   II. mixing the product mixture from I with an aqueous solution of an alkali metal hydroxide,
   III. feeding of the mixture from step II into a distillation column comprising at least an upper rectifying part ($VT^2$), a lower rectifying part ($VT^1$) and a stripping part (AT),
   IV. removing at least a portion of any bottom product in the region below the stripping part (AT),
   V. evaporating at least a portion of the bottom product removed in step IV in (i) a main evaporator and (ii) at least one downstream re-evaporator operated at a higher temperature than that of the main evaporator down to a residual aromatic amine content in the outflow of the re-evaporator of from 0 to 98 percent by weight, and
   VI. recycling completely any gas phase obtained in step V and partially recycling any liquid obtained in step V into the column, either below or above the stripping part, and partial or complete sluicing out of the liquid phase obtained in the re-evaporator.

2. The process of claim 1 in which the aromatic amine is aniline and the aromatic nitro compound is nitrobenzene.

3. The process of claim 1 in which the alkali metal hydroxide is used in the form of an aqueous solution having an alkali metal hydroxide content greater than 0.7 per cent by weight and less than or equal to 55 per cent by weight.

4. The process of claim 1 in which the alkali metal hydroxide is used in an amount within a range of $$0.01 < n(MOH)/[\Sigma\{i \cdot n(Ar(OH)_i)\}] < 1.5$$

in which
   n represents molar amount of substance,
   M represents an alkali metal,
   $Ar(OH)_i$ represents a compound with i phenolic hydroxyl groups and
   i represents a natural number.

5. The process of claim 4 in which the product from I is analyzed at regular intervals to determine the amount of aqueous alkali metal hydroxide solution needed to attain a desired concentration of compounds with phenolic hydroxyl groups.

6. The process of claim 1 in which the distillation column is operated under an absolute pressure of from 10 to 1,000 mbar and with a reflux ratio of from 0.05 to 3.

7. The process of claim 1 in which the re-evaporator is operated under the same pressure as the main evaporator.

8. The process of claim 1 in which the re-evaporator is suitable for processing of deposit-forming products.

9. The process of claim 1 in which the re-evaporator is flushed with water at regular intervals.

10. The process of claim 1 in which bottom outflow of the main evaporator is extracted with water and the organic washed phase is passed into the re-evaporator.

11. The process of claim 1 in which the distillation column is designed as a partition column.

* * * * *